United States Patent [19]

Lewnard et al.

[11] Patent Number: 5,218,003
[45] Date of Patent: Jun. 8, 1993

[54] LIQUID PHASE PROCESS FOR DIMETHYL ETHER SYNTHESIS

[75] Inventors: John J. Lewnard; Thomas H. Hsiung, both of Emmaus, Pa.; James F. White, Hudson, Ohio; Bharat L. Bhatt, Fogelsville, Pa.

[73] Assignee: Air Products and Chemicals, Inc., Allentown, Pa.

[21] Appl. No.: 873,493

[22] Filed: Apr. 23, 1992

Related U.S. Application Data

[63] Continuation of Ser. No. 602,988, Oct. 24, 1990, abandoned, which is a continuation-in-part of Ser. No. 381,450, Jul. 18, 1989, abandoned, which is a continuation-in-part of Ser. No. 143,799, Jan. 14, 1988, abandoned.

[51] Int. Cl.$^5$ .............................................. C07C 41/01
[52] U.S. Cl. ................................................ 518/700
[58] Field of Search ...................................... 518/700

[56] References Cited

FOREIGN PATENT DOCUMENTS 324475 7/1989 European Pat. Off. .
2093365 9/1982 United Kingdom .................. 518/713

OTHER PUBLICATIONS

Lewnard et al, Chemical Engineering Science, vol. 45, No. 8, pp. 2735-2741, 1990.
Hsiung et al, AIChE National Meeting, San Diego, Calif., Aug. 14-22, 1990, "Synthesis of Dimethyl Ether from Syngas in a Slurry Reactor".
Sherwin et al, Liquid Phase Methanol, AF-693 Research Project 317-2 May 1978.

*Primary Examiner*—Howard T. Mars
*Attorney, Agent, or Firm*—John M. Fernbacher; James C. Simmons; William F. Marsh

[57] ABSTRACT

A one-step process is disclosed for the coproduction of dimethyl ether and methanol from synthesis gas containing $H_2$, CO, and $CO_2$. The synthesis gas is contacted with a mixture of methanol synthesis and methanol dehydration catalysts suspended in an inert liquid in a three phase reactor system. Maximum dimethyl ether productivity and product energy recovery are realized by controlling the fraction of methanol synthesis catalyst in the range of about 75 to about 90 wt % of the total catalyst mixture. A methanol-rich fuel product containing dimethyl ether can be obtained when this range is about 95 to about 99.9 wt %.

10 Claims, 4 Drawing Sheets

LIQUID PHASE PROCESS FOR DIMETHYL ETHER SYNTHESIS

This is a continuation of copending application(s) Ser. No. 07/602,988 filed on Oct. 24, 1990 which is a continuation-in-part of U.S. Ser. No. 07/381,450 filed on Jul. 18, 1989, which is a continuation-in-part of U.S. Ser. No. 07/143,799 filed on Jan. 14, 1988 all now abandoned. The specifications of these continuation-in-part applications are incorporated herein by reference.

TECHNICAL FIELD

The present invention relates to a process for the production of dimethyl ether. More specifically, the present invention relates to a process for the direct production of dimethyl ether from synthesis gas using a three-phase reactor system.

BACKGROUND OF THE INVENTION

Conversion of synthesis gas to dimethyl ether requires three steps. Conventionally, synthesis gas is produced by reforming hydrocarbon or gasifying a carbon source such as coal or coke. Since this latter synthesis gas usually is too rich in CO to be used directly for dimethyl ether synthesis, an intermediate step is needed for conventional dimethyl ether manufacture. Consequently, the first step in the dimethyl ether synthesis is to adjust the composition of the synthesis gas via the water-gas shift reaction:

$$CO + H_2O \rightleftharpoons CO_2 + H_2 \quad (1)$$

After the ratio of hydrogen to carbon oxides has been adjusted, the gas is reacted to produce methanol (MeOH):

$$CO + 2H_2 \rightleftharpoons CH_3OH \quad (2)$$

Finally, methanol is dehydrated to form dimethyl ether (DME):

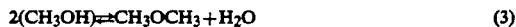

$$2(CH_3OH) \rightleftharpoons CH_3OCH_3 + H_2O \quad (3)$$

Reactions (1), (2), and (3) are equilibrium limited and exothermic. Moreover, the catalysts for both methanol synthesis and shift reactions are subject to severe deactivation when overheated. To avoid thermodynamic limitations and excessive catalyst deactivation, conventional gas phase reactors must be run at low per-pass conversions to maintain reactor temperature. Consequently, overall conversion of carbon monoxide to dimethyl ether is limited.

Multi-step processes, which use separate reactors for each reaction, cannot exploit the potential synergism of the three reactions. If these three reactions could be conducted simultaneously, methanol synthesis would drive the forward shift reaction, and dimethyl ether synthesis would drive both the methanol and shift reactions. Consequently, a one-step process is more flexible and can operate under a wider range of conditions than a multi-step process. In addition, multi-step processes require separate reactors, heat exchangers, and associated equipment for each reaction.

A single-step gas phase process would generally require less equipment than multi-step gas processes. However, a single-step gas-phase process would still suffer from a large reactor exotherm due to the high net heat of reaction. Hence, low per-pass conversions would be required to maintain reactor temperature to avoid a short catalyst life due to the large temperature rises associated with these reactions. Since the gas phase reactor is not isothermal, there are often severe equilibrium limitations in reactant conversions per pass.

Much of the prior art for dimethyl ether synthesis focuses on processes using improved catalysts to run shifted syngas ($H_2/CO$ greater than or equal to 1). Examples include U.S. Pat. Nos. 4,417,000; 4,423,155; 4,520,216; 4,590,176; and 4,521,540. These processes all run in the gas phase, and may be considered multi-step processes in that they all require the feed be shifted via Reaction (1).

Single-step gas-phase processes have been disclosed by Mobil Corp. and Haldor-Topsoe. For example, U.S. Pat. No. 4,011,275 assigned to Mobil Corp. discloses a gas-phase process for coproduction of methanol and dimethyl ether with $H_2$ deficient syngas feeds. Although there are no examples in the patent, the process is claimed to be useful for improving conversion of synthesis gas. U.S. Pat. No. 4,341,069 discloses a gas-phase process for dimethyl ether production to be used in conjunction with an integrated gasification combined cycle power plant. Examples in the patent show that the catalyst requires frequent regeneration, in some cases on a daily basis. Another gas-phase process is described in U.S. Pat. No. 4,481,305, however, this process is restricted to operation within a narrow range of $CO/CO_2$ ratio in the feed gas. It should be noted that efficient heat removal to maintain reactor temperature is generally not discussed in these patents. Fujimoto et al discusses in Chem. Letters, p.2051 (1984) the chemistry of the gas-phase one-step processes.

Combined methanol/dimethyl ether synthesis in the liquid phase has been reported by several workers. Sherwin and Blum, in their paper entitled "Liquid Phase Methanol Interim Report, May 1978", prepared for the Electric Power Research Institute, attempted to modify the liquid phase methanol process for coproduction of dimethyl ether by adding acid catalyst components to the system. They observed only traces of dimethyl ether, and concluded that the attempt was unsuccessful. Daroda, et al, J.C.S. Chem. Comm. p.1101 (1980), reported a broad slate of products for reactions of syngas with Fe in 2-methoxyethanol. However, in their system the solvent appears to act as a reactant, and the catalyst produces many side products. Consequently, neither earlier liquid phase process was economic.

UK Patent Application GB 2 093 365 A discloses the catalyst of above-cited U.S. Pat. No. 4,423,155 suitable for gas-phase synthesis of dimethyl ether, and discloses that such a catalyst may be suspended in a slurry for dimethyl ether synthesis in a liquid phase reactor.

An article by J. J. Lewnard et al entitled "Single-Step Synthesis of Dimethyl Ether in a Slurry Reactor" in *Chemical Engineering Science* Vol. 45, No. 8, pp. 2735–2741, 1990 describes the synthesis of dimethyl ether and methanol in a liquid phase reactor using synthesis gas feed containing between 20 and 60 vol % carbon monoxide. A mixed catalyst containing between 36 and 54 wt % methanol synthesis catalyst and the remainder methanol dehydration catalyst is disclosed. This synthesis is also described in a paper by T. H. Hsiung et al entitled "Synthesis of Dimethyl Ether from Syngas in a Slurry reactor" presented at the AIChE 1990 National Meeting, San Diego, Aug. 19–22, 1990.

SUMMARY OF THE INVENTION

The invention is a method for the production of dimethyl ether from synthesis gas containing hydrogen, carbon monoxide, and carbon dioxide which comprises contacting the synthesis gas with powdered catalyst slurried in an inert liquid in a liquid phase reactor and recovering therefrom a product containing dimethyl ether, wherein the powdered catalyst contains between about 70 and about 99.9 wt % methanol synthesis catalyst and the remainder of the powdered catalyst consists of methanol dehydration catalyst. The product from the reactor also contains methanol. When the powdered catalyst contains between about 75 and about 90 wt % methanol synthesis catalyst and the remainder of said powdered catalyst consists of methanol dehydration catalyst, the reactor productivity for dimethyl ether and the energy content of the product is maximized. When the powdered catalyst contains between about 95 and about 99.9 wt % methanol synthesis catalyst and the remainder of said powdered catalyst consists of methanol dehydration catalyst, the method yields a fuel product comprising methanol which contains between about 0.5 wt % and about 40 wt % dimethyl ether.

DETAILED DESCRIPTION OF THE INVENTION

Figure 1:
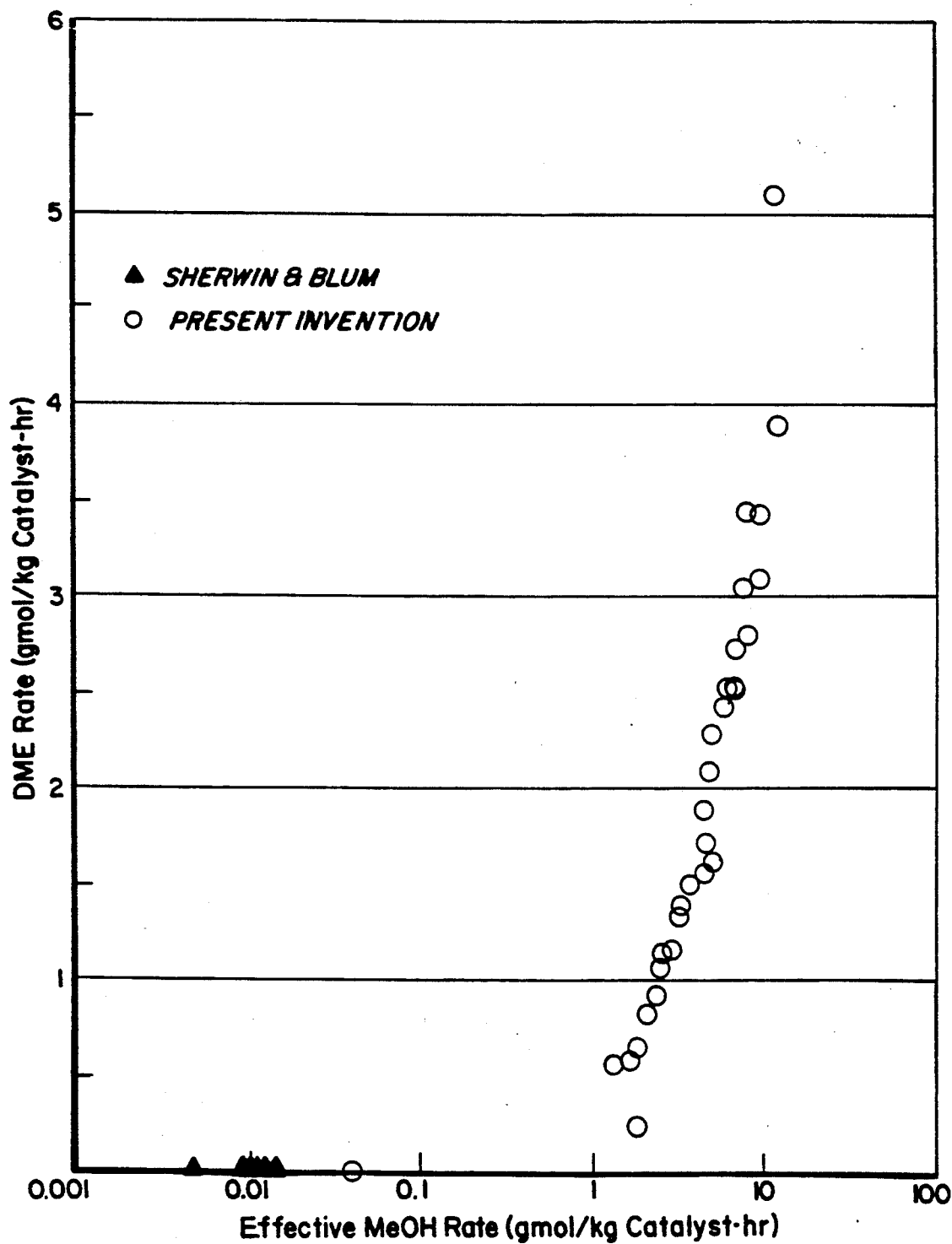
FIG. 1 is a plot of the rate of dimethyl ether formation versus the effective methanol rate.

The invention is a method for the production of dimethyl ether and methanol from synthesis gas containing hydrogen, carbon monoxide, and carbon dioxide which comprises contacting the synthesis gas with powdered catalyst slurried in an inert liquid in a liquid phase reactor and recovering therefrom a product containing dimethyl ether and methanol. Selectivity for dimethyl ether and methanol can be optimized by varying reaction conditions and/or catalyst compositions to suit specific end uses as described hereinafter. Mixtures of dimethyl ether and methanol can be used for their fuel value or for other applications based on specific chemical or physical properties. Dimethyl ether can be separated from the mixed product by known methods and recovered as a single product useful in a wide variety of applications.

The process uses a single catalyst mixture or a physical mixture of catalysts which can be in the form of shaped pellets or in the form of a fine powder, depending on the mode of operation. Many types of catalysts are known in the literature for each individual reaction of the process, and these can be mixed in various proportions in the reactor. The single catalyst mixture or physical mixture of catalysts must contain catalytic materials which promote both methanol synthesis and methanol dehydration. The reactor system can be either a single three phase reactor or a series of staged three phase reactors. Even though the process of the present invention can be carried out in a series of the staged three phase reactors, the dimethyl ether synthesis is carried out in a single step, i.e., all three reactions in the synthesis route are being driven simultaneously.

The process of the present invention can be operated in either an ebullated bed mode with a granulated (shaped pellet) catalyst having a typical pellet diameter of about $\frac{1}{8}''$ to $\frac{1}{4}''$, or a slurry mode with a powdered catalyst having a particle size of less than 200 microns. The concentration of catalyst in the liquid medium is in the range from about 5 wt % to about 60 wt %. As stated earlier, the single catalyst mixture or physical mixture of catalysts must contain catalytic materials which promote both methanol synthesis and methanol dehydration. The methanol synthesis catalytic material can for example comprise a typical copper-containing methanol synthesis catalyst. The dehydration catalytic material can be selected from the group consisting of alumina, silica-alumina, zeolites (e.g., ZSM-5), solid acids (e.g., boric acid), solid acid ion exchange resins (e.g., perflurorinated sulfonic acid) and mixtures thereof.

The preferred operating conditions of the process are a pressure range from about 200 psig to about 2000 psig. More preferably from about 400 psig to about 1500 psig; a temperature range from about 200° C. to about 350° C.; and a space velocity in excess of 50 standard liters of synthesis gas per kilogram of catalyst per hour, more preferably in the range from about 3,000 to about 15,000 standard liters of synthesis gas per kilogram of catalyst per hour. The process is particularly useful for higher CO content synthesis gases, even where the concentration of carbon monoxide in the synthesis gas is in excess of about 50 vol %.

The process can also comprise a further step of feeding water as a vapor of liquid to the three phase reactor with the synthesis gas feed. The addition of water is particularly beneficial when the concentration of hydrogen in the synthesis gas is less than 10 vol %. Total catalyst concentrations in the liquid medium can vary from very dilute, i.e., about 5 wt %, to very concentrated, i.e., about 60 wt % or higher. The catalyst is contained in an inert oil, such as a paraffinic hydrocarbon or a hydrocarbon blend. Other types of liquids are known to work for liquid phase processes, for example, oxygenated species such as alcohols, ethers, and polyethers. These oxygenated liquids should be inert, and have a boiling point for single component liquids or boiling range for blended liquids between 150° C. and 450° C.

In the process of the present invention, synthesis gas is introduced into the reactor and contacts the catalyst contained in the liquid medium. The synthesis gas is typically comprised of $H_2$, CO, $CO_2$, and often inert species such as $N_2$ and $CH_4$. The composition of the gas can vary widely, as shown in the Examples. Depending on feed concentrations of $H_2$, CO, and $CO_2$, it may be advantageous to co-feed $H_2O$ either as a liquid or vapor to the process in order to adjust the gas composition via the shift reaction. In addition, it may be advantageous to remove $CO_2$ from the feed gas in order to affect the dimethyl ether product selectivity. The removal of $CO_2$ can be accomplished by any conventional means, e.g., pressure swing adsorption or absorption using $CO_2$ selective solvents such as amines. The feed gas can be composed entirely of fresh feed in a once-through application, or it may be composed of a mixture of fresh feed and recycled gas.

Process conditions can vary widely, depending on operating conditions and type of reactor. Pressure ranges from ambient to high pressure since increasing pressure typically enhances synthesis. Preferred pressures range from about 200 to about 2000 psig, and more preferably about 400 to about 1500 psig. Temperature can range from about 200° C. to about 350° C., and preferably from 225° C. to 300° C.

Process conditions and yields are illustrated in the following Examples, which describe the use of various catalyst mixtures as well as single catalysts, and co-feed of $H_2O$. All runs were made in either a 300 cc or a 1 liter stainless steel autoclave with feed and product gas analysis via gas chromatograph. In all of the Examples (except Example 4), methanol synthesis catalyst was charged to the reactor along with the methanol dehydration catalyst and the inert liquid, and the methanol synthesis catalyst was reduced in situ. Runs were then carried out at varying process conditions for the given catalyst charge. In all of the Examples, space velocities and productivities are based on the total weight of the mixed catalyst charged to the system prior to reduction.

Although the following examples were carried out in a single three phase reactor, the process of the present invention can be carried out in a series of staged three phase reactors. Process conditions for the different reactors can be varied; however, the reactor conditions are not varied from reactor to reactor to isolate and accomplish a single reaction in the synthesis route. The process of the present invention is accomplished by simultaneously carrying out the three reactions of the dimethyl ether synthesis route.

EXAMPLE 1

The first series of experiments was performed with a balanced synthesis gas feed (55% $H_2$, 19% CO, 5% $CO_2$ 21% $N_2$) at 250° C. at 800 psig. A 25 wt % slurry consisting of 20 grams of powdered BASF S3-85 methanol synthesis catalyst (approximately 40 wt % CuO on a special support with an average particle size of less than 50 microns) and 20 grams of 200 mesh high purity gamma alumina (surface area of 250 $M^2$/gm, pore volume (0-100 Angstroms) of 0.45 cc/gm, prepared from boehmite sold under the tradename Catapal ® SB) was prepared in degassed Witco 70 oil. This oil is a 100% paraffinic hydrocarbon having a boiling range of 310 to 419° C.; a specific gravity of 0.845, a surface tension of 29.6 dynes/cm, and a viscosity of 19.5 cP, all at 25° C.; and a viscosity of 4.7 cP at 75° C. Results are shown in Table 1; methanol and dimethyl ether were the only detectable products. Comparison of CO conversions for methanol alone and dimethyl ether shows that the single-step dimethyl ether process is more efficient in overall CO conversion than production of methanol alone. In fact, Runs 1 and 2 show CO conversions greater than the thermodynamic maximum conversion for methanol alone.

$CO_2$ was found to have a major impact on dimethyl ether formation. Run 5, with no inlet $CO_2$, showed substantially higher dimethyl ether productivity and selectivity than Run 3. This comparison illustrates the potential for $CO_2$ removal from the feed gas.

TABLE 1

| Run | Feed | Temp (°C.) | GHSV (s−1/kg cat · hr) | Productivity (gmol/kg cat · hr) DME | MeOH | DME/MeOH Selectivity (mol %/mol %) | CO Conversion (mol %)[1] |
| --- | --- | --- | --- | --- | --- | --- | --- |
| 1 | Bal | 250 | 1500 | 2.3 | 1.6 | 60/40 | 69 (44) |
| 2 | Bal | 250 | 2500 | 3.2 | 2.6 | 55/45 | 55 (40) |
| 3 | Bal | 250 | 2750 | 2.8 | 3.0 | 49/51 | 52 (39) |
| 4 | Bal | 250 | 5000 | 3.6 | 4.2 | 46/54 | 36 (32) |
| 5 | Bal[2] | 250 | 2750 | 4.7 | 1.5 | 76/24 | 65 |

Note 1: Numbers in parentheses indicate carbon monoxide conversion observed for methanol synthesis in the absence of dimethyl ether synthesis.
Note 2: Balanced gas with no inlet $CO_2$ (57% $H_2$, 20% CO, 0% $CO_2$, 23% $N_2$)

EXAMPLE 2

To illustrate the use of a different catalyst mixture, and a different gas feed, a second series of experiments was made using 20 grams BASF S3-85 methanol catalyst (described in Example 1) and 40 grams of silica-alumina comprising 86 wt % silica and 13 wt % alumina having a surface area of 475 $M^2$/gm, sold as Davison Silica/Alumina MS 13/110, slurried in 120 grams of degassed Witco 70 oil (described in Example 1). Ten conditions were run with CO-rich and balanced gas at temperatures of 250° C. and ~265° C., and pressure of 800 psig. Results are shown in Table 2. Balanced gas has the same composition as Example 1, and CO-rich gas is comprised of 35% $H_2$, 51% CO, 13% $CO_2$, and 1% $N_2$.

TABLE 2

| Run | Feed | Temp (°C.) | GHSV (s−1/kg cat · hr) | Productivity (gmol/kg cat · hr) DME | MeOH | DME/MeOH Selectivity (mol %/mol %) |
| --- | --- | --- | --- | --- | --- | --- |
| 6 | Bal | 250 | 1870 | 2.46 | 0.96 | 72/28 |
| 7 | Bal | 250 | 3130 | 2.57 | 1.66 | 61/39 |
| 8 | Bal | 250 | 1120 | 1.92 | 0.57 | 77/23 |
| 9 | Bal | 263 | 1870 | 2.57 | 0.92 | 74/26 |
| 10 | Bal | 264 | 3730 | 3.09 | 1.45 | 68/32 |
| 11 | Bal | 265 | 1350 | 2.12 | 0.54 | 80/20 |
| 12 | CO-rich | 250 | 1870 | 1.41 | 0.42 | 77/23 |
| 13 | CO-rich | 250 | 1870 | 1.36 | 0.46 | 75/25 |
| 14 | CO-rich | 250 | 3130 | 1.18 | 0.59 | 66/34 |
| 15 | CO-rich | 250 | 1120 | 1.16 | 0.26 | 82/18 |

EXAMPLE 3

A third series of experiments illustrates operation with $H_2O$ co-feed, and simulataneous shift, methanol and dimethyl ether reactions. A 15 wt % slurry comprised of 25 grams of powdered BASF K3-110 commercial low-temperature shift catalyst (which is 40 wt % CuO, 40 wt % ZnO, balance $Al_2O_3$, and has a surface area of 100 $M^2/gm$), 25 grams BASF S3-85 (described in Example 1), and 25 grams high purity alumina (described in Example 1) was slurried in 425 grams degassed Witco 70 oil (described in Example 1). The pressure was 800 psig. The feed gas was 0.8% $H_2$, 57.7% CO, 15.5% $CO_2$, and balance $N_2$. Steam was co-fed with the gas to shift the CO and produce $H_2$. Results are summarized in Table 3.

ponent. In two separate trials, 15 g of powdered BASF S3-86 catalyst, which is CuO/ZnO on alumina, having an average particle diameter of less than 50 microns, and 15 g Davison silica alumina (defined in Example 2) were slurried in 100 g of Penreco Drakeol 10 (previously known as Sontex 100) mineral oil. This oil is a 65% paraffinic/35% naphthenic hydrocarbon having a boiling range of 283° C. (initial boiling point) to 419° C. (90% distilled per ASTM D1160); a specific gravity of 0.849, a surface tension of 30 dynes/cm, and a viscosity of 31.2 cP, all at 25° C.; and a flash point of 185° C. The

TABLE 3

| Run | Feed Ratio H2O/CO | Temp (°C.) | GHSV (s−1/kg cat · hr) | Productivity (gmol/kg cat · hr) DME | MeOH | DME/MeOH Selectivity (mol %/mol %) |
|---|---|---|---|---|---|---|
| 16 | 0.50 | 249 | 2000 | 0.40 | 2.19 | 16/84 |
| 17 | 0.33 | 247 | 1860 | 2.64 | 2.11 | 56/44 |

EXAMPLE 4

The next series of experiments illustrates the use of a single catalyst species in the process. A copper on alumina catalyst was prepared by dissolving 64.03 grams $Cu(NO_3)_2 \cdot 2.5H_2O$ in 100 ml deionized water. The solution was used to impregnate 78.14 grams $Al_2O_3$ in several portions, with $N_2$ purging between impregnations. The catalyst was dried overnight at 110° C., and reduced with 2% $H_2$. Following reduction, 25 grams catalyst (equivalent to 40.6 gram as oxide) were slurried in 100 grams of degassed Witco 70 oil. The system was run at 800 psig, and results are shown in Table 4.

TABLE 4

| Run | Feed | Temp (°C.) | GHSV (s−1/kg cat · hr) | Productivity (gmol/kg cat · hr) DME | MEOH | DME/MeOH Selectivity (mol %/mol %) |
|---|---|---|---|---|---|---|
| 18 | Bal | 249 | 3000 | 0.58 | 0.45 | 56/44 |
| 19 | Bal | 265 | 3000 | 0.82 | 0.41 | 67/33 |
| 20 | Bal | 296 | 3000 | 1.07 | 0.28 | 79/21 |

EXAMPLE 5

Another series of experiments illustrates the use of a catalyst mixture with a different methanol catalyst component.

autoclave was pressurized to 750 psig with CO-rich gas. Results are summarized in Table 5.

TABLE 5

| Run | Temp (°C.) | GHSV (s−1/kg cat · hr) | Productivity (gmol/kg cat · hr) DME | MeOH | DME/MeOH Selectivity (mol %/mol %) |
|---|---|---|---|---|---|
| 21 | 250 | 1500 | 2.80 | 2.33 | 55/45 |
| 22 | 250 | 733 | 1.50 | 0.62 | 71/29 |
| 23 | 250 | 1500 | 2.73 | 1.32 | 67/33 |
| 24 | 250 | 1425 | 2.28 | 0.34 | 87/13 |
| 25 | 250 | 2163 | 1.61 | 1.81 | 47/53 |
| 26 | 260 | 1925 | 1.71 | 1.16 | 60/40 |
| 27 | 260 | 1500 | 2.42 | 0.89 | 73/23 |
| 28 | 260 | 733 | 0.56 | 0.21 | 73/23 |
| 29 | 260 | 1620 | 0.65 | 0.48 | 58/42 |
| 30 | 250 | 860 | 0.92 | 0.50 | 65/35 |

A second series of experiments using BASF S3-86 catalyst was conducted, and the results are given in Table 6. The effective methanol rate was deliberately decreased by injecting 4 g of chloride as NaCl to the slurry in Runs 34 and 35. This decreased the effective methanol rate below the threshold value, and consequently decreased the dimethyl ether rate to nil.

TABLE 6

| Run | Temp (°C.) | GHSV (s−1/kg cat · hr) | Productivity (gmol/kg cat · hr) DME | MeOH | DME/MeOH Selectivity (mol %/mol %) |
|---|---|---|---|---|---|
| 31 | 250 | 2075 | 3.44 | 1.12 | 75/25 |
| 32 | 250 | 773 | 1.50 | 0.62 | 77/29 |
| 33 | 250 | 1500 | 2.73 | 1.32 | 67/33 |
| 34 | 250 | 2075 | 0.00 | 0.04 | 0/100 |
| 35 | 270 | 1300 | 0.00 | 0.00 | — |

EXAMPLE 6

A series of experiment was carried out using the laboratory procedure of the previous Examples to study the effects of the ratio of methanol synthesis catalyst to methanol dehydration catalyst on product composition.

Figure 3:
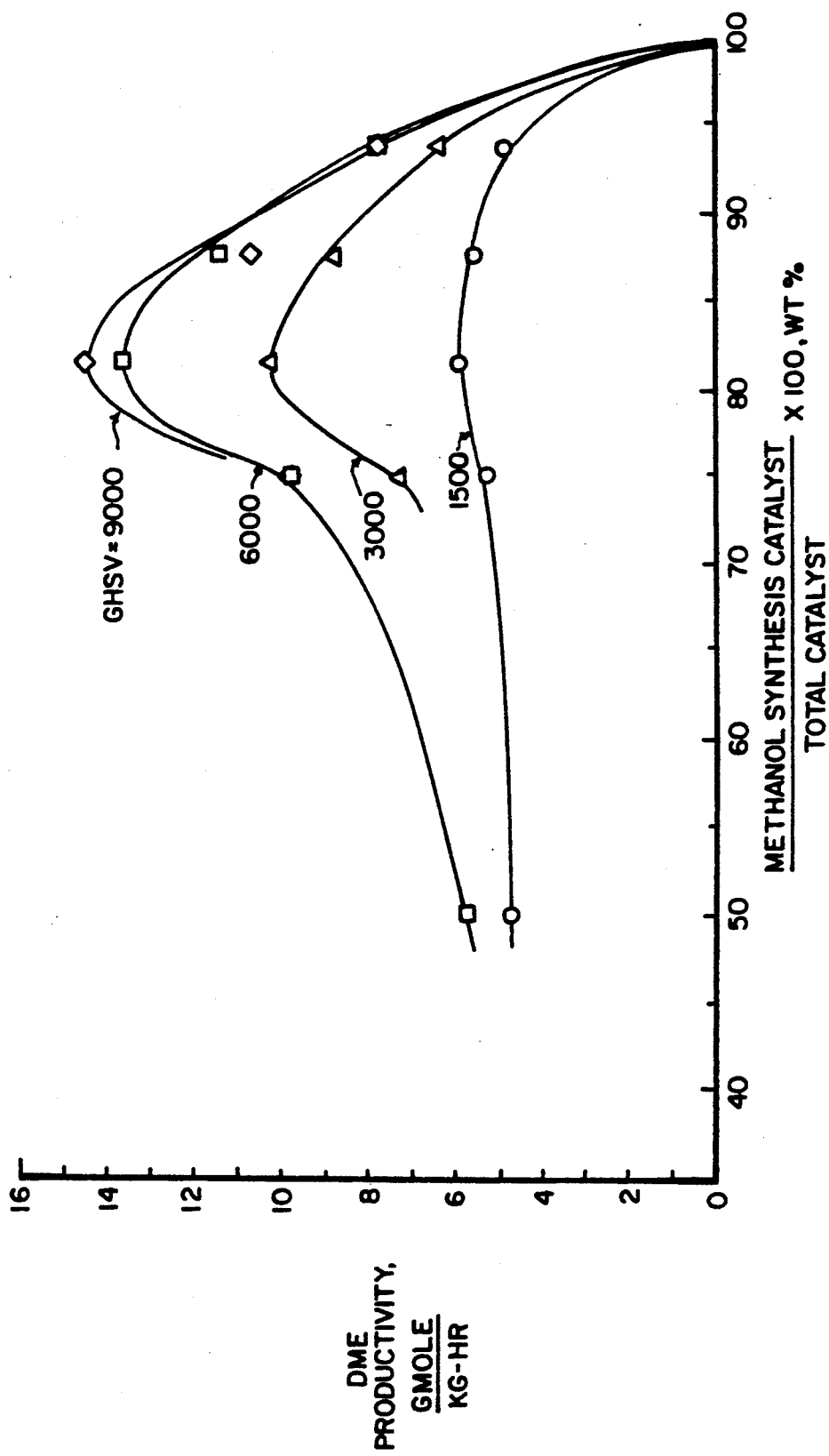
FIG. 3 is a plot of dimethyl ether reactor productivity versus wt % methanol synthesis catalyst in the total catalyst.
Figure 4:
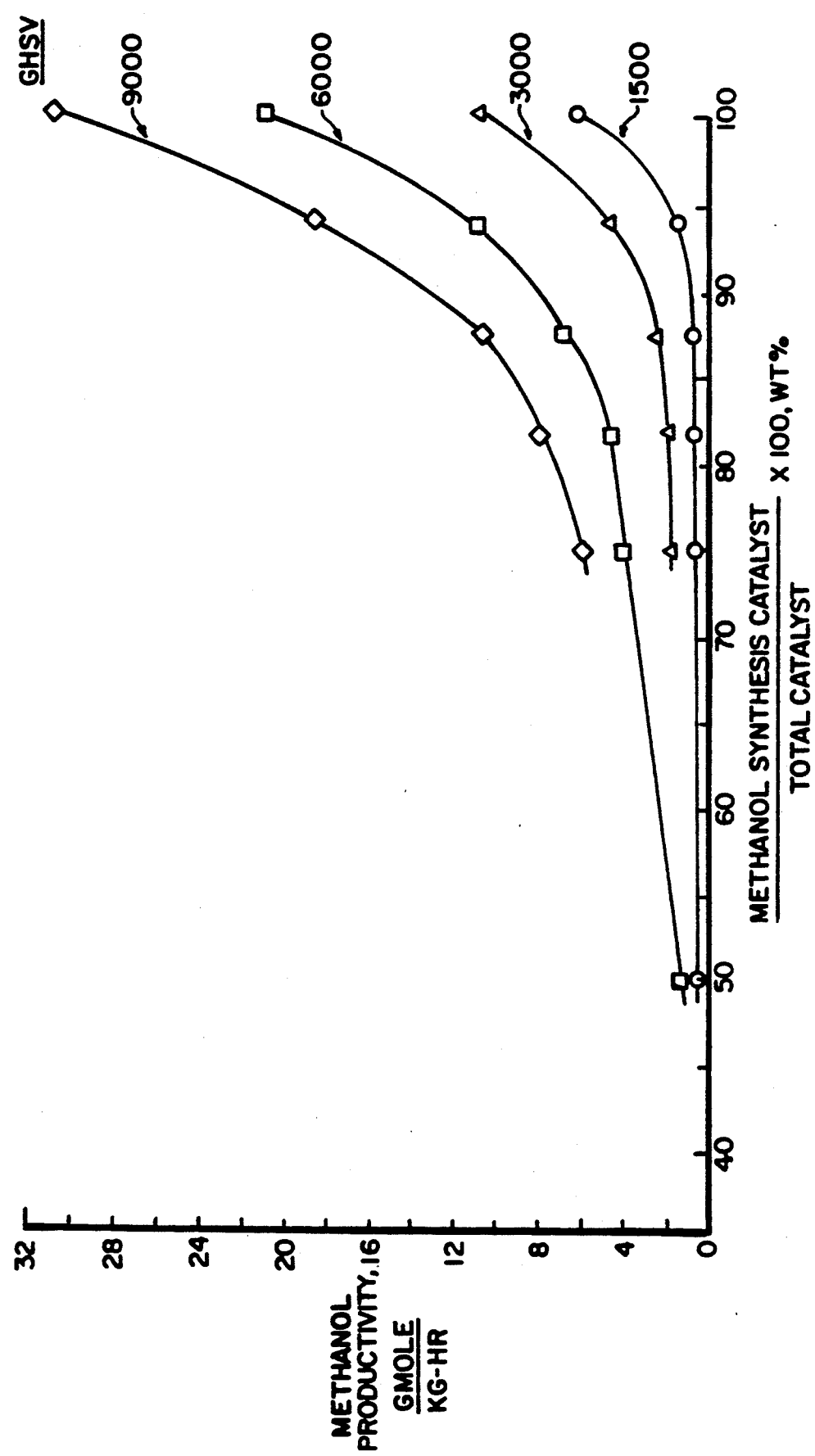
FIG. 4 is a plot of methanol reactor productivity versus wt % methanol synthesis catalyst in the total catalyst.

All runs were made at 250° C. and 750 psig with a total catalyst slurry concentration of 20 wt%. The synthesis gas feed had the following composition: 51 mol % CO, 35% $H_2$, and 1% $N_2$. The same methanol synthesis catalyst of Example 5 was used for these runs; a methanol dehydration catalyst was prepared by heating boehmite (alumina monohydrate, $Al_2O_3 \cdot H_2O$) powder at a rate sufficient to increase the temperature of the alumina by about 100° C/hr to about 500° C., maintaining the temperature of the alumina at 500° C. for about 3 hours, and cooling the resulting heat-treated alumina to ambient temperature. Gas hourly space velocities (GSHV) were varied from 1500 to 9000 std liters/kg catalyst-hr) and the percent of methanol synthesis catalyst in the total catalyst was varied between 50 and 100 wt%. The results of these experiments are shown as plots of dimethyl ether and methanol productivity versus wt % methanol synthesis catalyst in FIGS. 3 and 4 respectively. FIG. 3 shows that the dimethyl ether productivity exhibits a maximum at about 81 wt % methanol synthesis catalyst for the particular catalysts and operating conditions of these experiments. This is a new discovery not predictable from the previously-cited prior art.

The foregoing examples demonstrate that a useful single-step process for the coproduction of methanol and dimethyl ether from synthesis gas requires two essential features. First, the effective rate of methanol synthesis must exceed a minimum threshold value. Second, it is essential to have a catalyst or catalyst mixture which contains individual catalytic materials which promote both methanol synthesis and methanol dehydration reactions. It has been discovered as shown in Example 6 that a sharp maximum in dimethyl ether productivity occurs as the relative amounts of methanol synthesis and dehydration catalysts are varied. Thus it is possible to control and optimize product properties by controlling the relative catalyst composition in the liquid phase reactor.

Because methanol is the key intermediate reactant in this process, its rate of production has an important effect on the overall process performance. This point can be illustrated by defining the effective methanol rate or effective rate of methanol synthesis, $r^*_{MeOH}$, as:

$$r^*_{MeOH} = r_{MeOH} + 2(r_{DME})$$

where $r_{MeOH}$ and $r_{DME}$ are the rates of methanol and dimethyl ether formation, respectively, measured with respect to the total quantity of catalyst in the process.

The present invention clearly demonstrates that there is a certain minimum value of $r^*_{MeOH}$ that is necessary in order to produce significant quantities of dimethyl ether. Below this threshold value, at best only trace quantities of dimethyl ether will be formed. FIG. 1, which plots $r_{DME}$ versus $r^*_{MeOH}$ calculated from the data of the present invention (Examples 1-5) and Sherwin et al., shows that the minimum effective methanol rate ($r^*MeOH$) is about 1.0 gmol/(kg catalyst • hr). Thus, FIG. 1 clearly explains why Sherwin et al., whose results are shown as closed triangles, where unsuccessful in their attempt to produce dimethyl ether. These experiments were all operated below the threshold limit of the effective methanol rate, and hence yielded only trace quantities of dimethyl ether. The results for the present invention, shown as open circles, confirm that the quantity of dimethyl ether produced is essentially nil at these low effective methanol rates. However, the dimethyl ether rate increases rapidly once the minimum threshold rate is achieved. The data confirm this conclusion for the process using several different catalyst systems, feeding several synthesis gases with a wide range of compositions, and operating over a wide range of temperatures and pressures. Hence a useful commercial process to produce dimethyl ether from synthesis gas must operate at or above the threshold rate.

Figure 2:
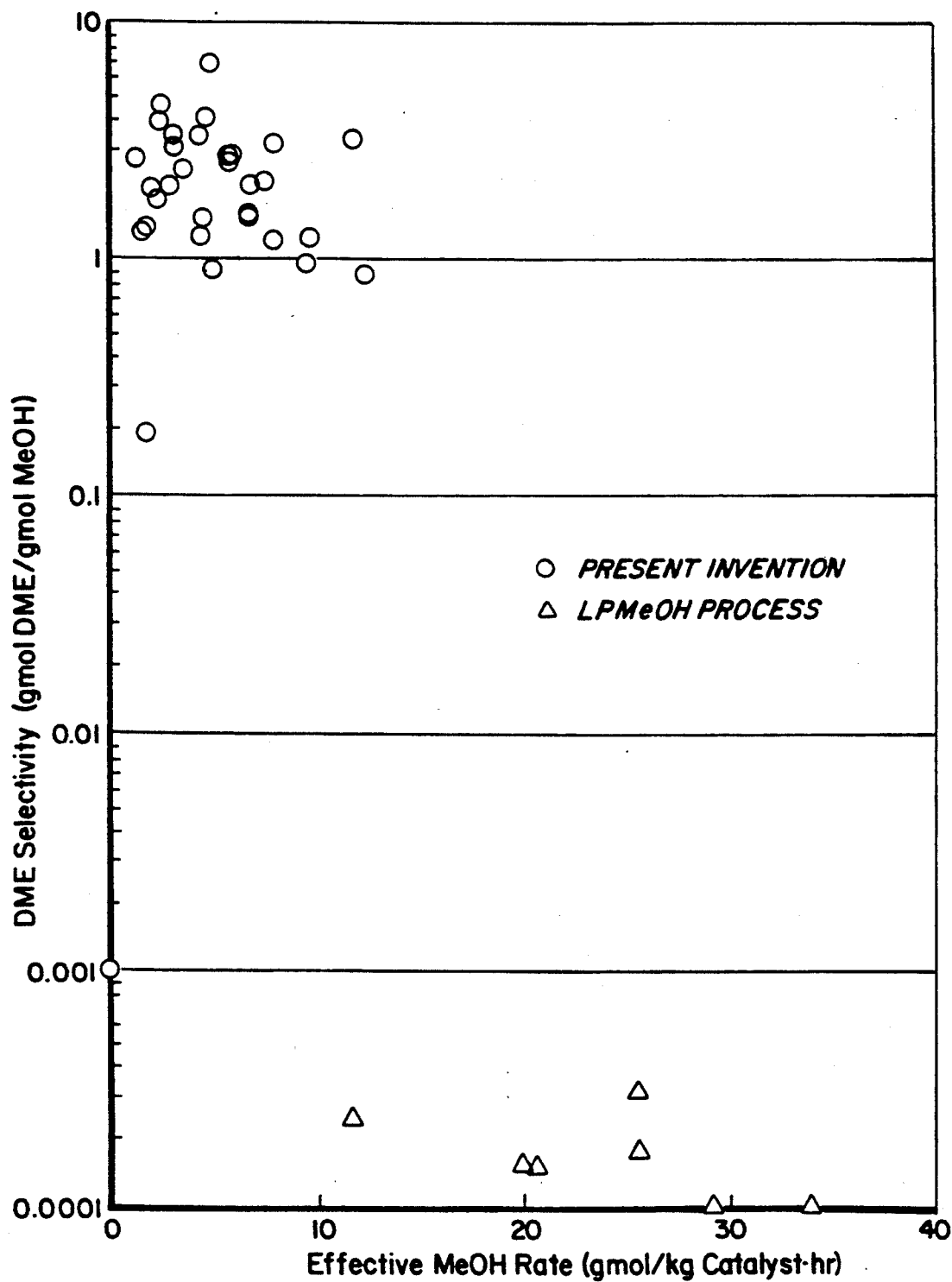
FIG. 2 is a plot of dimethyl ether selectivity versus the effective methanol rate.

An essential aspect of the present invention is that the catalyst or catalyst mixture must contain individual catalytic materials which promote both methanol synthesis and methanol dehydration reactions. It is well known that all process for production of methanol from synthesis gas yield trace quantities of dimethyl ether. However, these trace quantities are too small to constitute a commercially viable process for the production of dimethyl ether. Dimethyl ether is produced is significant quantity only when both methanol synthesis and methanol dehydration catalyst components are present. FIG. 2 confirms this observation by comparing results at similar operating conditions for the liquid phase dimethyl ether process, in which both catalyst components are present (shown as open circles), to the liquid phase methanol process, in which only methanol synthesis catalyst is present (shown as open triangles). Dimethyl ether selectivity, defined as the moles of dimethyl ether produced divided by the moles of methanol produced, is shown as a function of the effective methanol rate. As discussed above, the amount of dimethyl ether produced is very low below this threshold rate. Above this rate, dimethyl ether production is significant in the process of the present invention, since the effective methanol rate is greater than the threshold value. However, dimethyl ether production is insignificant in the liquid phase methanol process over the entire range of operation because the dehydration catalyst component is not present.

In order to obtain the minimum effective methanol rate the traditional operating parameters of temperature, pressure, catalyst type, and oil type can be manipulated; the catalyst particle size also appears to have a significant effect on the amount of dimethyl ether produced by the process of the present invention. The earlier work by Sherwin et al. recites some catalysts of unspecified size and others with sizes from 0.85 to 1.20 mm in diameter; the work of the present invention utilizes catalysts with particle diameters below 200 microns, and preferably below 10 microns. The process of the present invention produced significant quantities of dimethyl ether; the process as taught by Sherwin et al. made only trace quantities of dimethyl ether.

The present invention solves the previously described problems in dimethyl ether production from synthesis gas via methanol dehydration through two important features of the process. First, the liquid medium acts as a heat sink, resulting in isothermal operation for the reactor. This factor is critical since the forward shift, methanol synthesis, and dimethyl ether synthesis reactions are all exothermic. With conventional gas-phase processes, the heat released during reaction increases temperature, which impedes reaction due to thermodynamic limitations, and causes catalyst deactivation. The high thermal capacity of the liquid phase permits high conversions while maintaining stable temperatures. This excellent temperature control may be responsible for increased catalyst life of this process relative to gas phase operations which require frequent catalyst regeneration. Second, the present invention uniquely exploits the synergism of the chemistry of all three reactions by combining them in a single step. By combining the three reactions in a simultaneous process, each of the individual reactions is driven thermodynamically by removing its inhibiting products as reactants for the subsequent reaction. For example, the first series of experiments showed CO conversions for the DME process which exceed the thermodynamic maximum for methanol synthesis alone. Such synergism cannot be achieved in multi-step process, where each reaction proceeds at most to its individual thermodynamic limitation in separate reactors. Also, since all reactions in the process of the present invention proceed simultaneously, the process permits several options for varying the product distribution by manipulating the extent of each reaction. As discussed earlier, the DME/MeOH selectivity can be controlled by varying the relative amount or activity of the catalyst constituents in the liquid phase reactor. The product distribution can also be varied by changing reaction conditions such as space velocity, temperature, pressure or feed compositions.

Although several prior art processes involve of combinations of reactions (1) through (3), the reactions were conducted in the gas phase as earlier discussed. Since the shift and methanol synthesis reactions are thermodynamically limited by high temperatures and all three reactions are exothermic, removal of heat from the reactor is a critical and probably the limiting factor in their design. The significance of the thermal control provided by the liquid phase is best illustrated by comparing gas and liquid phase processes. For example, the adiabatic temperature rise for a gas-phase process providing the same conversions as the conditions of Run 1 is 350° C., versus a liquid phase process with an actual temperature rise less than 10° C. due to the presence of the liquid phase. No current commercial catalyst could function economically at a gas phase adiabatic temperature of 600° C. without heat removal equipment or product gas recycling. Both options are generally very expensive. For example, using product gas recycling to control the temperature rise would require a recycle ratio in the range of 10 to 20. Such high recycle ratios require high capital investments for compressors and reactors, as well as high operating costs. In comparison, a liquid phase unit would require little or no feed recycle, and a much smaller reactor. Hence liquid phase synthesis can provide economic operation at high conversions.

Another distinguishing feature of the invention is that the simultaneous shift, methanol synthesis, and DME synthesis reactions enable the process to use synthesis gas feeds with wide ranges in composition. Previously disclosed processes can only operate within restricted ranges of $H_2/CO$ or $CO/CO_2$ ratios. This invention demonstrates operation with feeds richer in CO than any previous processes. For example, Runs 16 and 17 in Example 3 show high productivity with feed CO concentrations of 58% and a $H_2/CO$ ratio below 0.02. Such conditions are well beyond those claimed or taught for the prior art processes.

The composition and thus the properties of the methanol-dimethyl ether coproduct can be controlled in the present invention by selecting the relative amounts of the two catalysts in the liquid phase reactor. As illustrated in Example 6, the dimethyl ether productivity exhibits a maximum at about 81 wt % methanol synthesis catalyst. The exact location of this maximum will depend upon the specific catalysts used and the reactor operating conditions, and occurs between about 70 and about 95 wt %, and most likely between about 75 and about 90 wt %, of the methanol synthesis catalyst relative to the total catalyst in the reactor. The remainder of the catalyst is methanol dehydration catalyst as earlier described. This maximum in dimethyl ether productivity also corresponds to a maximum energy content of the product and thus a maximum energy recovery relative to the synthesis gas feed. This is so because dimethyl ether has about double the heat of combustion of methanol. Thus if it is desired to produce dimethyl ether as a final product or to maximize the energy content of the product relative to that of the synthesis gas feed, the liquid phase reactor should be operated with a catalyst mixture which contains between about 75 and about 90 wt % methanol synthesis catalyst and the remainder methanol dehydration catalyst. It is also possible to produce a methanol-rich fuel product containing between about 0.5 and 40 wt % dimethyl ether by operating the reactor with between about 95 and about 99.9 wt % methanol synthesis catalyst with the remainder methanol dehydration catalyst. Such a product can be useful for example as a motor fuel in which the selected amount of dimethyl ether controls the desired octane and vapor pressure properties of the fuel.

The present invention thus allows the efficient coproduction of methanol and dimethyl ether using a wide range of synthesis gas feed compositions in a single liquid phase reactor. By controlling the relative amounts of methanol synthesis and methanol dehydration catalysts in the reactor, different product compositions can be obtained at selected reactor operating conditions.

The essential characteristics of this invention are described fully and completely in the foregoing disclosure, from which one skilled in the art can understand the invention and make various changes and modifications thereto without departing from the basic spirit and scope thereof..

We claim:

1. A method for the coproduction of dimethyl ether and methanol from synthesis gas containing hydrogen, carbon monoxide, and carbon dioxide which comprises contacting said synthesis gas with powdered catalyst slurried in an inert liquid in a liquid phase reactor and recovering therefrom a product containing said dimethyl ether, wherein said powdered catalyst contains between about 75 and about 90 wt % copper-containing methanol synthesis catalyst and the remainder of said powdered catalyst consists essentially of methanol dehydration catalyst selected from the group consisting of alumina, silica-alumina, zeolites, solid acids, solid acid ion exchange resins, and mixtures thereof, and further wherein the gas hourly space velocity (GHSV) in said liquid phase reactor is between 3000 and 15,000 standard liters/(kg catalyst-hr).

2. The method of claim 1 wherein water is introduced into said liquid phase reactor along with said synthesis gas.

3. The method of claim 1 wherein said liquid phase reactor is operated at conditions such that the minimum effective methanol rate is greater than about 1.0 gmol methanol/(kg catalyst.hr).

4. The method of claim 1 wherein said powdered catalyst has an average particle size of less than about 200 microns.

5. The method of claim 1 wherein the concentration of said powdered catalyst in said inert liquid is between about 5 and about 60 wt %.

6. The method of claim 1 which further comprises operating said liquid phase reactor at a reactor pressure between about 200 and about 2000 psig.

7. The method of claim 1 which further comprises operating said liquid phase reactor at a reactor pressure between about 400 and about 1500 psig.

8. The method of claim 1 which further comprises operating said liquid phase reactor at a temperature between about 200° C. and about 350° C.

9. The method of claim 1 wherein said synthesis gas contains greater than about 50 mol % carbon monoxide.

10. The method of claim 1 wherein said methanol dehydration catalyst is alumina and is prepared by heating boehmite (alumina monohydrate, $Al_2O_3 \cdot H_2O$) powder at a rate sufficient to increase the temperature of said alumina by about 100° C./hr to about 500° C., maintaining the temperature of said alumina at about 500° C. for about 3 hours, and cooling the resulting heat-treated alumina to ambient temperature.

* * * * *